(12) United States Patent (10) Patent No.: US 12,636,065 B2
Shen et al. (45) Date of Patent: May 26, 2026

(54) MONOPOLAR L-HOOK ELECTRODE WITH VARIED CROSS-SECTIONS

(71) Applicant: Covidien LP, Mansfield, MA (US)

(72) Inventors: Tong Shen, Shanghai (CN); Yongming Zhao, Shanghai (CN); Yuan Kang, Shanghai (CN); Peng Zha, Shanghai (CN); Xinmeng Liu, Shanghai (CN); Lijun Zhu, Shanghai (CN); Xiaoxin Wang, Shanghai (CN)

(73) Assignee: Covidien LP, Mansfield, MA (US)

( * ) Notice: Subject to any disclaimer, the term of this patent is extended or adjusted under 35 U.S.C. 154(b) by 574 days.

(21) Appl. No.: 18/018,948

(22) PCT Filed: Jul. 31, 2020

(86) PCT No.: PCT/CN2020/106199
§ 371 (c)(1),
(2) Date: Jan. 31, 2023

(87) PCT Pub. No.: WO2022/021324
PCT Pub. Date: Feb. 3, 2022

(65) Prior Publication Data
US 2023/0301704 A1 Sep. 28, 2023

(51) Int. Cl.
*A61B 18/14* (2006.01)
*A61B 18/00* (2006.01)

(52) U.S. Cl.
CPC .... *A61B 18/14* (2013.01); *A61B 2018/00107* (2013.01); *A61B 2018/1422* (2013.01)

(58) Field of Classification Search
CPC ................ A61B 18/14; A61B 18/1482; A61B 2018/00083; A61B 2018/00107; A61B 2018/0013; A61B 2018/00136; A61B 2018/00607; A61B 2018/1405; A61B 2018/1422; A61B 2018/167
See application file for complete search history.

(56) References Cited

U.S. PATENT DOCUMENTS

| | | | |
|---|---|---|---|
| 2004/0267254 A1 | 12/2004 | Manzo et al. | |
| 2006/0106379 A1 | 5/2006 | O'Brien et al. | |
| 2011/0054461 A1* | 3/2011 | Dickhans | A61B 18/148 |
| | | | 606/41 |

(Continued)

FOREIGN PATENT DOCUMENTS

| | | |
|---|---|---|
| CN | 201175374 Y | 1/2009 |
| CN | 102939055 A | 2/2013 |

(Continued)

OTHER PUBLICATIONS

International Search Report and Written Opinion of the International Searching Authority issued in corresponding application PCT/CN2020/106199 mailed Apr. 29, 2021 (8 pages).

(Continued)

*Primary Examiner* — Tigist S Demie
(74) *Attorney, Agent, or Firm* — Carter, DeLuca & Farrell, LLP

(57) ABSTRACT
An electrosurgical hook electrode includes an intermediate portion (36), a hook portion (38) connected to the intermediate portion (36) at a bend angle, and a coating (40) disposed over the intermediate portion (36) and the hook portion (38), the coating (40) having a varying thickness.

20 Claims, 5 Drawing Sheets

(56) References Cited

U.S. PATENT DOCUMENTS

2011/0184410  A1    7/2011  Greep et al.
2020/0060751  A1    2/2020  Bonn

FOREIGN PATENT DOCUMENTS

CN        110141359  A    8/2019
CN        110856665  A    3/2020
CN        111166468  A    5/2020

OTHER PUBLICATIONS

Extended European Search Report issued in corresponding appli-
cation EP 20947665.4 dated Feb. 26, 2024 (8 pages).

* cited by examiner

MONOPOLAR L-HOOK ELECTRODE WITH VARIED CROSS-SECTIONS

CROSS REFERENCE TO RELATED APPLICATIONS

The present application is a U.S. National Stage Application filed under 35 U.S.C. § 371(a) of International Patent Application No. PCT/CN2020/106199, filed Jul. 31, 2020. The entire disclosure of the foregoing application is incorporated by reference herein.

BACKGROUND

Technical Field

The present disclosure relates to an electrosurgical electrode and, more particularly, to an electrosurgical electrode having an L-hook shape with varied cross-section to enable precise delivery of RF energy during laparoscopic surgery.

Background of Related Art

Electrosurgery involves application of high radio frequency (RF) electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

The traditional monopolar electrodes apply radiofrequency electrical energy to heat the tissue to transect or achieve hemostasis. There is a need for a coating which can reduce the unexpected thermal damage and secondary damage caused by tissue adhesion.

Monopolar L-hook electrode is the most frequently selected device in colorectal obstetrics gynecological, urological, and bariatric surgeries due to its high efficiency and low cost. Thus, there is a need for a modified L-hook shaped electrode that limits thermal damage to tissue.

SUMMARY

Monopolar L-hook electrode according to the present disclosure utilizes the RF electrical energy to heat the tissue to transect or achieve hemostasis. In most dissection cases, surgeons use the inside surface of monopolar L-Hook electrode to hook target tissue, then pull in a proximal direction to apply tension and activate RF power simultaneously until tissue is dissected. In other cases, surgeon use the outside of monopolar L-Hook electrode to touch target tissue, then push distally to apply tension against tissue and activate RF power simultaneously. When operating on tough tissue (e.g., bundle, tendons, etc.) surgeon has to apply higher pull or push forces against the tension of tissue, which causes the risk of accidental tissue damage. To avoid such dangerous operation, surgeons are prone to use higher power setting, which may cause unintended cauterization of tissue. The design of a monopolar L-hook electrode according to the present disclosure may be used at lowest power setting to achieve equal or better dissection performance to meet the needs of precise surgeries.

The present disclosure provides a monopolar L-hook electrode having a varied cross-section, which provides better dissection performance during lower power activation. The proposed design leverages the shape of monopolar L-hook electrode and extends the functions to enable precise operation with minimal thermal damage and lower RF energy coursing through patient.

According to one embodiment of the present disclosure, an electrosurgical electrode is disclosed. The electrosurgical electrode includes an intermediate portion, a hook portion connected to the intermediate portion at a bend angle, and a coating disposed over the intermediate portion and the hook portion, the coating having a varying thickness.

According to one aspect of the above embodiment, the electrosurgical electrode further includes a proximal portion that is in parallel relative to the intermediate portion and a slanted portion connected to the proximal portion at an obtuse angle. The intermediate portion is connected to the slanted portion at an inverse angle of the obtuse angle. The bend angle may be from about 80° to about 88°.

According to another aspect of the above embodiment, the coating may be formed from a dielectric material formed from at least one of a polymer or a ceramic material. The coating may be also formed from a dielectric polymer selected from the group consisting of polytetrafluoroethylene and perfluoroalkoxy alkane polymer. The coating may be further formed from a dielectric ceramic material selected from the group consisting of titanium nitride, chromium nitride, and aluminum oxide.

According to a further aspect of the above embodiment, the hook portion includes a tip having an elliptical cross section at a distal end portion thereof. A cross-section of a distal end portion of the hook portion includes an inner curved portion and an outer curved portion and two surfaces extending from the inner curved at a proximal angle from about 40° to about 60°. The inner curved portion has a radius from 0.02 mm to about 0.1 mm that is smaller than a radius of the outer curved portion. The coating has a thinner thickness at the inner curved portion and the outer curved portion than in other areas of the distal end portion. The thickness may be from about 1 μm to 10 μm.

According to yet another aspect of the above embodiment, a cross-section of a proximal end portion of the hook portion includes an inner curved portion and an outer curved portion and two surfaces extending from the inner curved at a distal angle from about 80° to about 100°. The inner curved portion has a radius from 0.02 mm to about 0.1 mm that is smaller than a radius of the outer curved portion. The coating has a thinner thickness at the inner curved portion and the outer curved portion than in other areas of the proximal end portion. The thinner thickness is from about 1 μm to 10 μm.

According to one aspect of the above embodiment, a cross-section of a distal end portion of the hook portion includes an inner curved portion having a first radius and an outer curved portion having a second radius that is smaller than the first radius.

BRIEF DESCRIPTION OF THE DRAWINGS

The present disclosure may be understood by reference to the accompanying drawings, when considered in conjunction with the subsequent, detailed description, in which.

DETAILED DESCRIPTION

Figure 1:
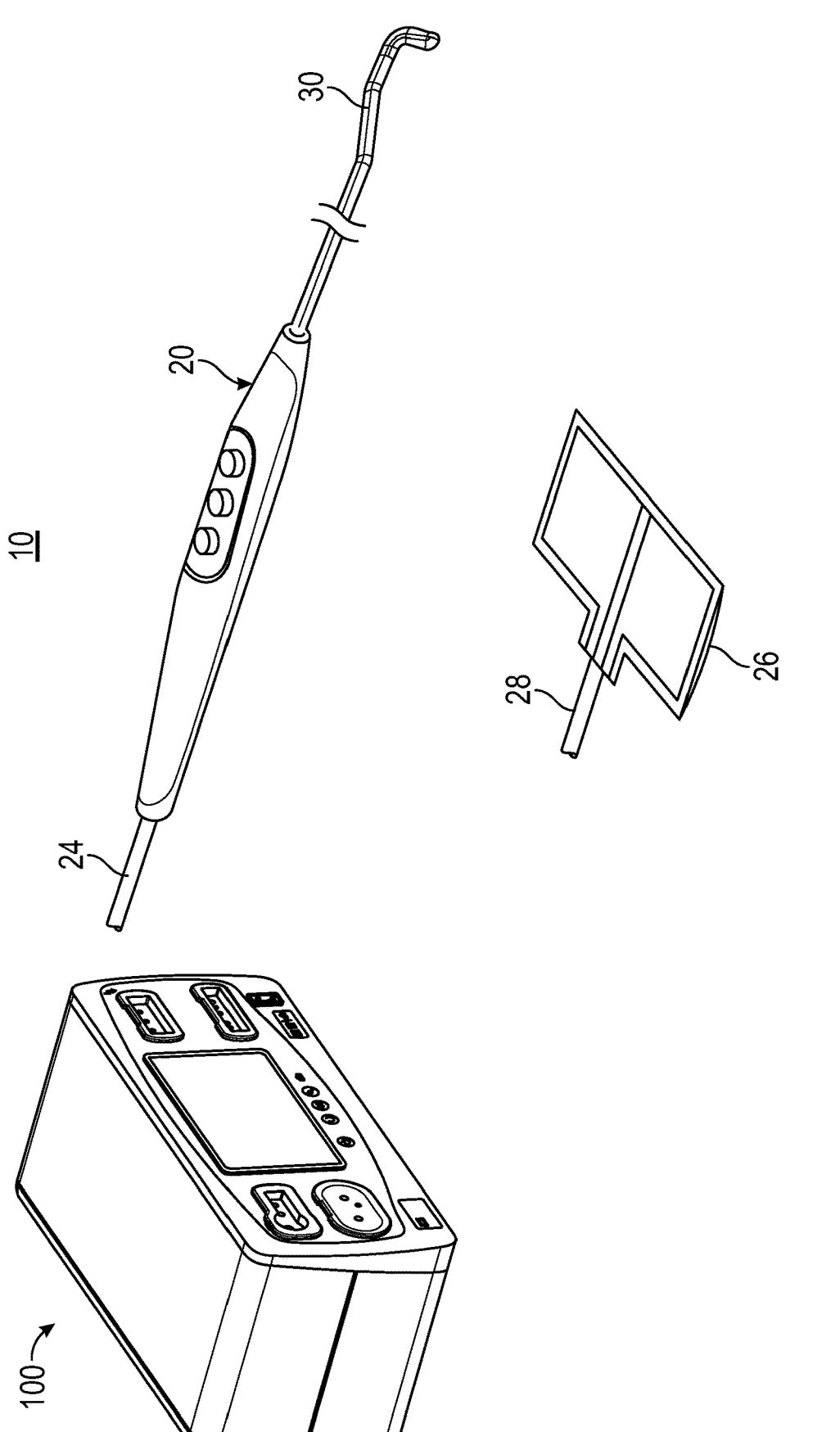
FIG. 1 is a perspective view of an electrosurgical system according to an embodiment of the present disclosure.

Embodiments of the presently disclosed electrosurgical system are described in detail with reference to the drawings, in which like reference numerals designate identical or corresponding elements in each of the several views. As used herein the term "distal" refers to the portion of the surgical instrument coupled thereto that is closer to the patient, while the term "proximal" refers to the portion that is farther from the patient.

In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

Referring to FIG. 1 an electrosurgical system 10 for use with an electrosurgical instrument having an electrode according to the present disclosure, such as a monopolar electrosurgical instrument 20. Monopolar electrosurgical instrument 20 includes an active electrode 30 (e.g., electrosurgical cutting blade, etc.) for treating tissue of a patient. The system 10 may include a plurality of return electrode pads 26 that, in use, are disposed on a patient to minimize the chances of tissue damage by maximizing the overall contact area with the patient. Electrosurgical alternating RF current is supplied to the monopolar electrosurgical instrument 20 by a generator 100 via supply line 24. The alternating RF current is returned to the generator 100 through the return electrode pad 26 via a return line 28.

Figure 2:
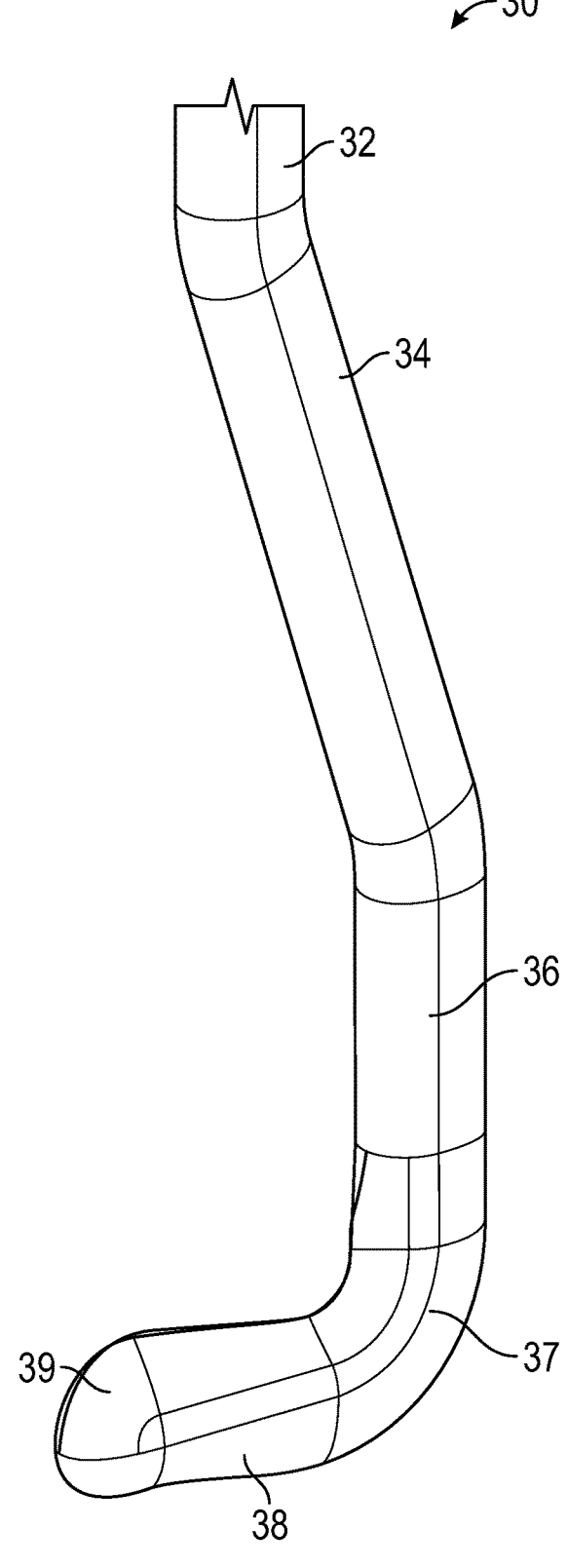
FIG. 2 is a perspective view of an electrode according to an embodiment of the present disclosure.
Figure 3:
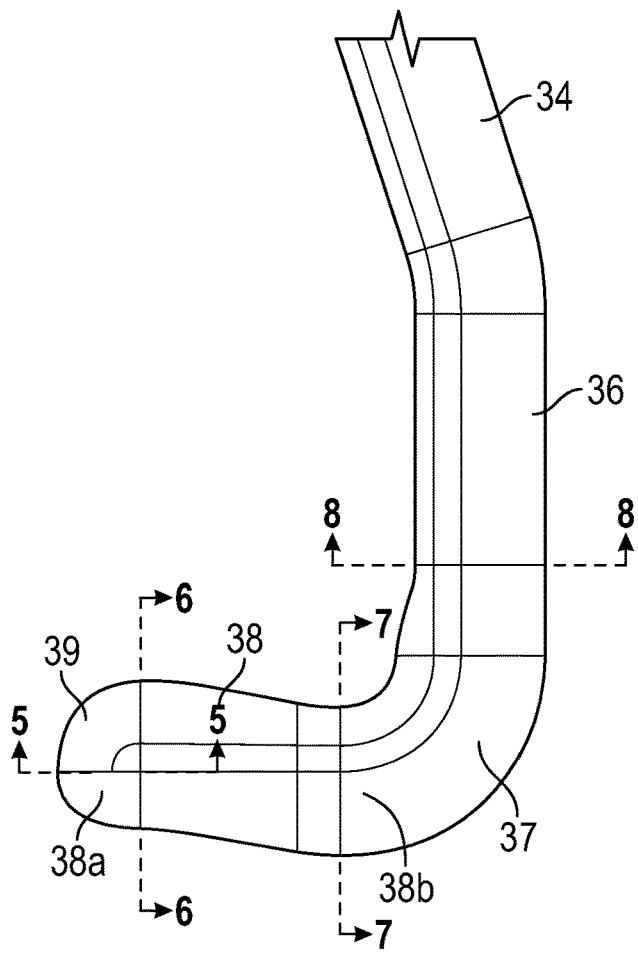
FIG. 3 is a side view of the electrode of FIG. 2 according to an embodiment of the present disclosure.
Figure 4:
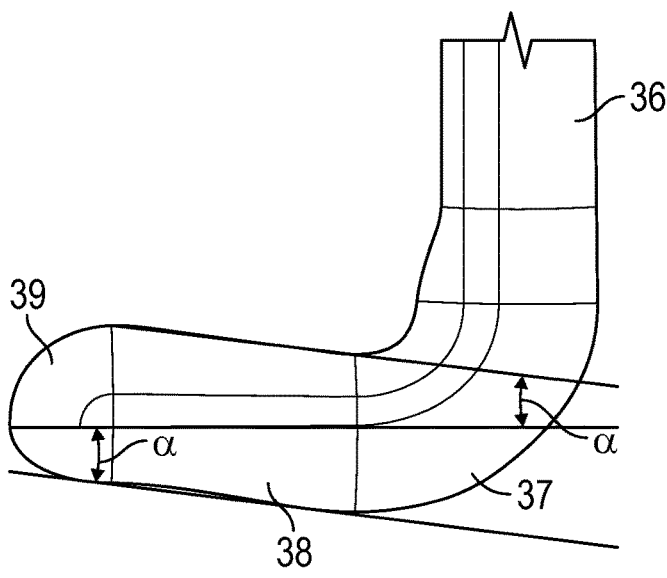
FIG. 4 is an enlarged, side view of the electrode of FIG. 2 according to an embodiment of the present disclosure.

With reference to FIG. 2, the electrode 30 is formed from a conductive type material, such as, stainless steel. The electrode 30 may be formed using any suitable metal forming technique such as computer numeral control machining process or metal injection molding. The electrode 30 includes a proximal end portion 32, a slanted portion 34, which is disposed at an obtuse angle, relative to the proximal end portion 32, which may be from about 110° to about 160°. With reference to FIGS. 2-4, the slanted portion 34 is connected to an intermediate potion 36, which may be parallel to the proximal end portion 32 and may be disposed at an inverse angle of the obtuse angle relative to the slanted portion 32.

The electrode 30 also includes a hook portion 38 coupled to the intermediate portion 36 via a bend 37. As shown in FIG. 4, the hook portion 38 is disposed at an angle α, which may be from about 2° to about 10° from the perpendicular orientation (e.g., from 88° to 80°) relative to the intermediate portion 36. The angle α allows for easier hooking of tissue. The hook portion 38 also includes a tip 39 at a distal end portion 38a, which allows for quicker breakdown of hooked tissue when activating RF energy and causing the rest of the tissue to slip into the inside of the bend 37 between the hook portion 38 and the intermediate portion 36 such that the tissue is transected. The slant beam design also reduces tissue contact area during the procedure to achieve higher current concentration, thus, accelerating the dissection procedure and reducing the operational force.

With reference to FIGS. 5-8, cross-sectional views of the electrode at sectional lines 5-5, 6-6, 7-7, 8-8, illustrate changing cross-sectional geometry of the electrode 30 and in particular, the intermediate portion 36 and the hook portion 38. The electrode 30 includes an insulative coating 40 (FIGS. 5-8), which may be formed from any dielectric material, such as a polymer, a ceramic, or combinations thereof. The coating 40 has a high impedance to RF energy and provides anti-stickiness performance at high temperature, e.g., about 300° C. Suitable polymers include polytetrafluoroethylene (PTFE), perfluoroalkoxy alkane (PFA) polymers and suitable ceramics include titanium nitride, chromium nitride, aluminum oxide, and the like. The thickness of the coating 40 varies across different surfaces as shown in FIGS. 5-8.

Figure 5:
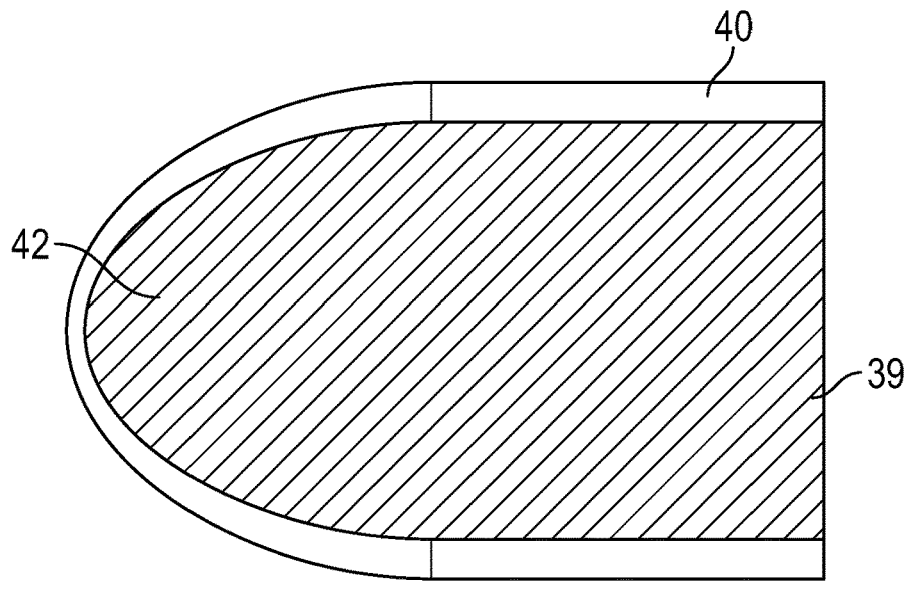
FIG. 5 is a longitudinal cross-sectional view of the electrode of FIG. 2 taken along a cross-sectional line 5-5.

FIG. 5 shows the longitudinal cross-section of the tip 39, which has a semi-elliptical projection profile 42 and is designed to cause higher current concentration than traditional semi-circular profiles when activated by RF energy. The semi-elliptical curvature is non-sharp to prevent physical damage when surgeon is performing blunt dissection. The thickness of the coating 40 close to the horizontal vertices of the ellipse is thinner and may be from about 1 μm to 10 μm and is less than the thickness of the coating that is closer to the vertical, which may be from about 20 μm to 50 μm.

Figure 6:
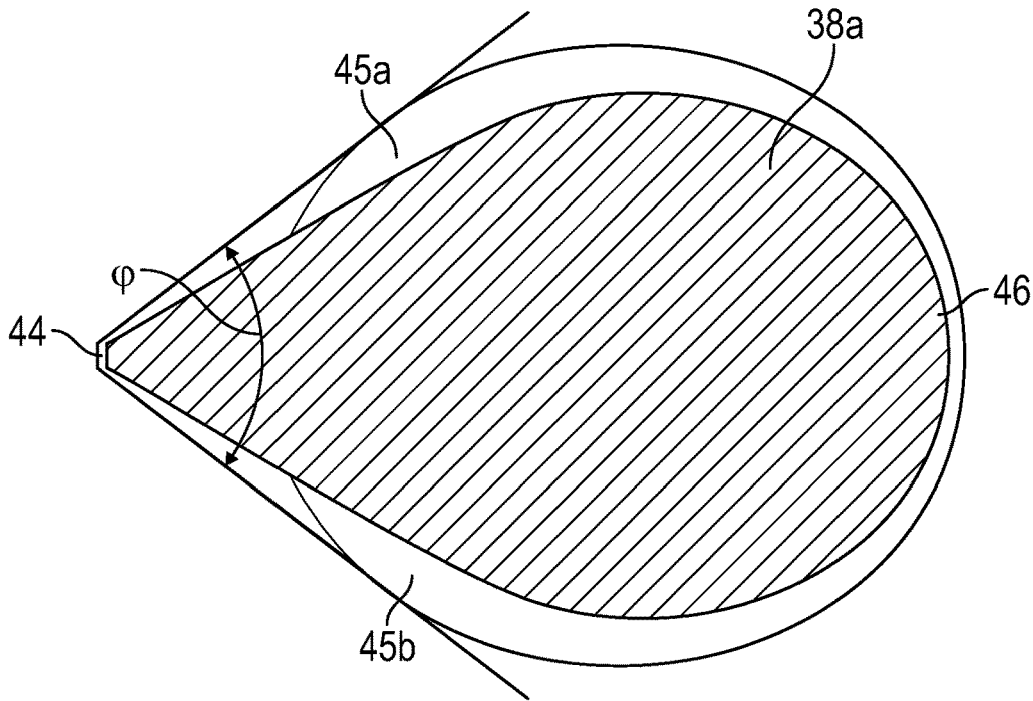
FIG. 6 is a side cross-sectional view of the electrode of FIG. 2 taken along a cross-sectional line 6-6.

FIG. 6 shows a transverse cross-section at the distal end portion 38a of the hook portion 38, which has a water-drop shape. The distal end portion 38a has an inner curved portion 44, an outer end portion 46, and two flat surfaces 45a and 45b disposed at a sharp angle φ (FIG. 3), which may be from about 40° to about 60°. The angle is designed to cause high current concentration when activated by RF energy. The inner curved portion 44 has a radius from about 0.02 mm to about 0.1 mm that is smaller than the radius of the outer curved portion 46 and forms the main emission area of RF energy. The outer curved portion 46 is blunt to prevent causing physical damage and concentrates current at the inner curved portion 44. The thickness of the coating 40 close to the horizontal vertices of the ellipse (i.e., inner curved portion 44 and the outer curved portion 46) is thinner and may be from about 1 μm to 10 μm and is less than the thickness of the coating that is closer to the vertical, which may be from about 20 μm to 50 μm.

Figures 7, 8:
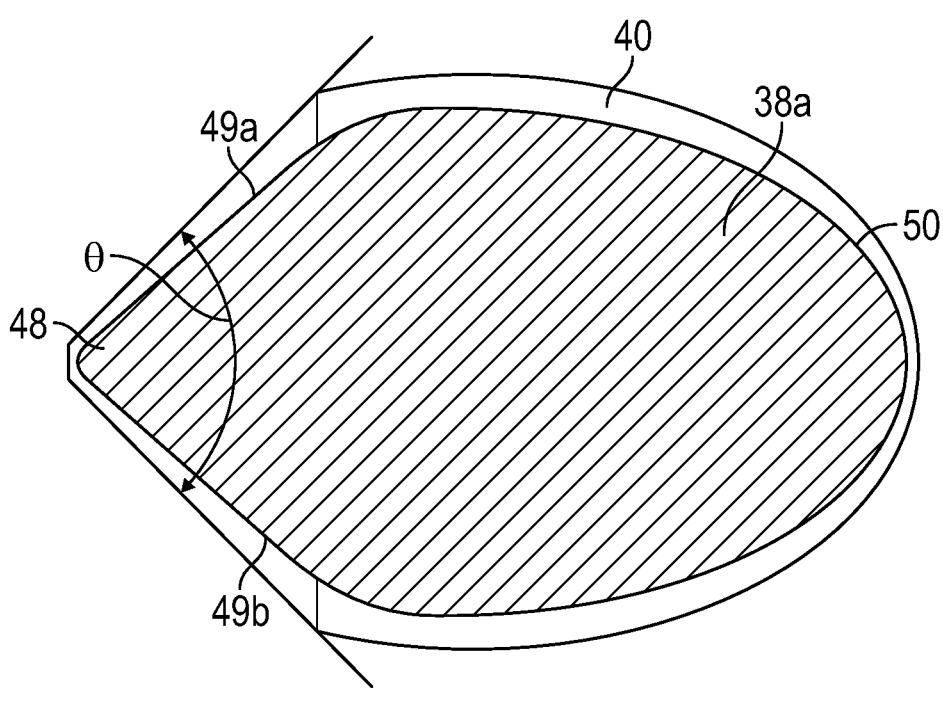
FIG. 7 is a side cross-sectional view of the electrode of FIG. 2 taken along a cross-sectional line 7-7.
FIG. 8 is a side cross-sectional view of the electrode of FIG. 2 taken along a cross-sectional line 8-8.

FIG. 7 shows a transverse cross-section of the hook portion 38 at a proximal end portion adjacent to the bend 37. The cross-section of a proximal end portion 38b (FIG. 3) has a modified water-drop shape. The proximal end portion 38a also has an inner curved portion 48, an outer curved portion 50, and two flat surfaces 49a and 49b disposed at an angle θ, which may be from about 80° to about 100°. The angle is also designed to cause high current concentration when activated by RF energy, but to a lesser degree than the angle φ.

The inner curved portion 48 may have a radius from about 0.02 mm to about 0.1 mm that is smaller than the radius of the outer curved portion 50 and forms the main emission area of RF energy. The semi-elliptical curvature of an outer curved portion 50 is designed to cause higher current concentration than traditional semi-circular profile while blunt enough to prevent physical damage. The shape of the outer curved portion 50 also improves outside dissection performance. The thickness of the coating 40 close to the horizontal vertices of the ellipse (i.e., inner curved portion 48 and the outer curved portion 50) is thinner and may be from about 1 μm to 10 μm and is less than the thickness of the coating that is closer to the vertical, which may be from about 20 μm to 50 μm.

FIG. 8 shows a transverse cross-section of the intermediate portion 36, which has an inner curved portion 52 and an outer curved portion 54. The inner curved portion 52 has a semi-elliptical curvature outside and the outer curved portion 54 has semi-circular curvature. The outer curved portion 54 is designed to cause higher current concentration while blunt enough to prevent physical damage and improves outside dissection performance when RF energy is activated. The inner curved portion 52 is also designed to be blunt to avoid causing physical damage and has a radius that is larger than the radius of the outer curved portion 54. The outer curved portion 54 forms the main emission area of RF energy.

The inner curved portion 52 balances out the outer curved portion 52 and allows the outer curved portion 54 to concentrate current, thus, reversing the current concentration from inside to outside, unlike the hook portion 38, which concentrates current on the inside surface as described about with respect to FIGS. 6 and 7. The thickness of the coating 40 close to the horizontal vertices of the ellipse (i.e., inner curved portion 52 and the outer curved portion 54) is thinner and may be from about 1 μm to 10 μm and is less than the thickness of the coating that is closer to the vertical, which may be from about 20 μm to 50 μm.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical electrode comprising:
an intermediate portion;
a hook portion connected to the intermediate portion at a bend angle; and
a coating disposed over the intermediate portion and the hook portion, the coating having a varying thickness, wherein a cross-section of a proximal end portion of the hook portion includes an inner curved portion and an outer curved portion and two surfaces extending from the inner curved portion at a distal angle from about 80° to about 100°.

2. The electrosurgical electrode according to claim 1, further comprising:
a proximal portion that is in parallel relative to the intermediate portion; and
a slanted portion connected to the proximal portion at an obtuse angle, wherein the intermediate portion is connected to the slanted portion at an inverse angle of the obtuse angle.

3. The electrosurgical electrode according to claim 1, wherein the coating is formed from a dielectric material formed from at least one of a polymer or a ceramic material.

4. The electrosurgical electrode according to claim 1, wherein the coating is formed from a dielectric polymer selected from the group consisting of polytetrafluoroethylene and perfluoroalkoxy alkane polymer.

5. The electrosurgical electrode according to claim 1, wherein the coating is formed from a dielectric ceramic material selected from the group consisting of titanium nitride, chromium nitride, and aluminum oxide.

6. The electrosurgical electrode according to claim 1, wherein the hook portion includes a tip having an elliptical cross section at a distal end portion thereof.

7. The electrosurgical electrode according to claim 1, wherein a cross-section of a distal end portion of the hook portion includes an inner curved portion and an outer curved portion and two surfaces extending from the inner curved at a proximal angle from about 40° to about 60°.

8. The electrosurgical electrode according to claim 7, wherein the inner curved portion of the cross-section of the distal end portion of the hook portion has a radius from 0.02 mm to about 0.1 mm that is smaller than a radius of the outer curved portion of the cross-section of the distal end portion of the hook portion.

9. The electrosurgical electrode according to claim 7, wherein the coating has a thinner thickness at the inner curved portion of the cross-section of the distal end portion of the hook portion and the outer curved portion of the cross-section of the distal end portion of the hook portion than in other areas of the distal end portion.

10. The electrosurgical electrode according to claim 9, wherein the thinner thickness is from about 1 μm to 10 μm.

11. The electrosurgical electrode according to claim 1, wherein the inner curved portion has a radius from 0.02 mm to about 0.1 mm that is smaller than a radius of the outer curved portion.

12. The electrosurgical electrode according to claim 11, wherein the coating has a thinner thickness at the inner curved portion and the outer curved portion than in other areas of the proximal end portion.

13. The electrosurgical electrode according to claim 12, wherein the thinner thickness is from about 1 μm to 10 μm.

14. The electrosurgical electrode according to claim 1, wherein a cross-section of a distal end portion of the hook portion includes an inner curved portion having a first radius and an outer curved portion having a second radius that is smaller than the first radius.

15. The electrosurgical electrode according to claim 1, wherein the bend angle is from about 80° to about 88°.

16. An electrosurgical electrode comprising:
an intermediate portion;
a hook portion connected to the intermediate portion at a bend angle; and
a coating disposed over the intermediate portion and the hook portion, the coating having a varying thickness, wherein a cross-section of a proximal end portion of the hook portion includes an inner convex curved portion and an outer convex curved portion and two surfaces extending from the inner convex curved portion at a distal angle from about 80° to about 100°.

17. The electrosurgical electrode according to claim 16, wherein the inner convex curved portion defines a radius of curvature less than a radius of curvature of the outer convex curved portion.

18. The electrosurgical electrode according to claim 16, wherein the coating increases in thickness along a portion of an outer surface of the hook portion from an apex of the inner convex curved portion towards the outer convex curved portion.

19. The electrosurgical electrode according to claim 16, wherein the coating increases in thickness along a portion of an outer surface of the hook portion from an apex of the outer convex curved portion towards the inner convex curved portion.

20. The electrosurgical electrode according to claim 16, wherein the coating increases in thickness along a first portion of an outer surface of the hook portion from an apex of the inner convex curved portion towards the outer convex curved portion, and wherein the coating increases in thickness along a second portion of an outer surface of the hook portion from an apex of the outer convex curved portion towards the inner convex curved portion.

\* \* \* \* \*